(12) United States Patent
Menzel et al.

(10) Patent No.: US 8,815,961 B2
(45) Date of Patent: Aug. 26, 2014

(54) METHOD OF AND PLANT FOR MAKING A METHANE-CONTAINING GAS FROM SYNGAS

(75) Inventors: Johannes Menzel, Waltrop (DE); Holger Thielert, Dortmund (DE)

(73) Assignee: Thyssenkrupp Uhde GmbH, Dortmund (DE)

( * ) Notice: Subject to any disclaimer, the term of this patent is extended or adjusted under 35 U.S.C. 154(b) by 56 days.

(21) Appl. No.: 13/702,864

(22) PCT Filed: Jul. 12, 2011

(86) PCT No.: PCT/EP2011/061893
§ 371 (c)(1),
(2), (4) Date: Mar. 27, 2013

(87) PCT Pub. No.: WO2012/013493
PCT Pub. Date: Feb. 2, 2012

(65) Prior Publication Data
US 2013/0237617 A1    Sep. 12, 2013

(30) Foreign Application Priority Data
Jul. 28, 2010 (DE) .......................... 10 2010 032 528

(51) Int. Cl.
| C07C 27/00 | (2006.01) |
| B01J 8/04 | (2006.01) |
| B01J 19/00 | (2006.01) |
| C07C 1/04 | (2006.01) |
| C10L 3/08 | (2006.01) |
| C10G 2/00 | (2006.01) |

(52) U.S. Cl.
CPC .......... *C07C 1/04* (2013.01); *C10G 2300/4012* (2013.01); *C07C 1/0485* (2013.01); *C10G 2300/1022* (2013.01); *C10G 2300/4081* (2013.01); *C10L 3/08* (2013.01); *C10G 2/32* (2013.01)
USPC ............................ 518/700; 422/647; 422/198

(58) Field of Classification Search
CPC ............... C10G 2300/4012; C10G 2300/4081; C10G 2/32; C07C 1/0485; C07C 1/04; C10L 3/08
USPC .................................. 518/700; 422/647, 198
See application file for complete search history.

(56) References Cited

U.S. PATENT DOCUMENTS
4,130,575 A    12/1978    Jorn

FOREIGN PATENT DOCUMENTS
GB    2231040 A    11/1990

*Primary Examiner* — Jafar Parsa
(74) *Attorney, Agent, or Firm* — Andrew Wilford

(57) ABSTRACT

The invention relates to a process for producing a methane-containing gas from synthesis gas, wherein a synthesis gas containing carbon monoxide and hydrogen is fed for methanation to a reactor system (1) having a catalyst material, wherein the process gas stream leaving the reactor system (1) is divided into a product gas stream and a recycle gas stream, and wherein the recycle gas stream, for compensation of the pressure drop, is transported through an ejector (5) and for cooling is passed together with the synthesis gas into the reactor system (1). According to the invention, the product gas stream is compressed to a pressure which is greater than the pressure of the synthesis gas that is fed to the reactor system (1). Either compressed product gas or industrial gas from an industrial gas pipe system (9) is fed as propellant medium to the ejector (5). The invention also relates to a methane production plant for carrying out the process.

7 Claims, 1 Drawing Sheet

METHOD OF AND PLANT FOR MAKING A METHANE-CONTAINING GAS FROM SYNGAS

CROSS REFERENCE TO RELATED APPLICATIONS

This application is the US-national stage of PCT application PCT/EP2011/061893 filed 12 Jul. 2011 and claiming the priority of German patent application 102010032528.7 itself filed 28 Jul. 2010.

The invention relates to a method of making a methane-containing gas from synthesis gas, where
- a synthesis gas containing carbon monoxide and hydrogen is supplied to a reactor including a catalyst to effect methanation,
- the process gas stream leaving the reactor is divided into a product-gas stream and a recycle-gas stream,
- the recycle-gas stream is moved through an ejector and passed into the reactor (1) to be cooled.

The method enables, for example solids such as coal, biomass in the form of wood and straw, as well as various liquid carbon-containing educts to be converted into synthetic natural gas that can be fed into a natural-gas transmission network. Conversion of carbon monoxide and hydrogen to form methane is effected first by the equation

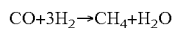
$$CO + 3H_2 \rightarrow CH_4 + H_2O$$

In addition, the following equilibrium reaction must be taken into account

$$CO + H_2O \leftrightarrows CO_2 + H_2$$

with the result that methane is also generated by the reaction:

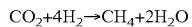
$$CO_2 + 4H_2 \rightarrow CH_4 + 2H_2O$$

The methanation in the presence of a catalyst proceeds in a highly exothermic fashion. At the same time, the disadvantage results whereby the methane yield decreases with increasing temperature due to the reaction equilibria. In order to cool the reactor, the approach is therefore known whereby the process gas stream leaving the reactor is divided into a product-gas stream and a recycle-gas stream and the previously cooled recycle gas is then returned to the inlet of the reactor. When the recycle gas is recirculated, the pressure drops that occur must be compensated for. Using a compressor for this purpose creates the problem that it can only be designed for increased temperatures of around 300° C. at considerable cost, and for this reason the process gas stream leaving the reactor is typically cooled down significantly such that water contained in the process gas stream also condenses.

GB 1 516 319 [U.S. Pat. No. 4,130,575] discloses an approach whereby a jet pump, also called an ejector, is used to convey the recycle-gas stream and to compensate pressure drops. The ejector is of simple construction and can be readily operated at elevated temperatures of, for example 300° C. The synthesis gas or steam supplied to the reactor is provided as the motive medium of the ejector. When synthesis gas is used as the motive medium, it undergoes a pressure drop in the ejector, with the result that the methanation is effected in the reactor at a reduced pressure. Due to the equilibria of the methanation reactions, there is also a reduced methane yield due to the reduction in pressure and this then also reduces the efficiency of the method. Using steam as the motive medium is disadvantageous since this approach accelerates the aging process for typical catalysts.

In light of this background, the object of this invention is to provide a method of making a methane-containing gas from synthesis gas, which method can be carried out with increased efficiency and at reduced cost.

Based on a method having the features described above, the object is attained according to the invention by an approach wherein the product-gas stream is compressed to a pressure that is greater than the pressure of the synthesis gas supplied to the reactor, such that either the thus compressed product gas, or a useful gas from a useful-gas conduit system, is fed to the ejector as the motive medium.

In order to supply the product gas for subsequent use, compression is applied so that a portion of this compressed product gas becomes the motive medium of the ejector in a first embodiment of the invention. The disadvantages that occur in the prior art—specifically, a reduction in the pressure of the synthesis gas or an accelerated aging of the catalyst—can thus be prevented.

After pressurization, the portion of the product gas that is not used as motive medium can be stored, for example in a pressure tank or transferred to a useful-gas conduit system. Thus the invention enables, in particular, synthetic natural gas to be produced that after further compression can be fed into a natural-gas transmission network. The pressure in this type of useful-gas conduit system typically ranges between 60 and 80 bar, whereas the synthesis gas introduced into the reactor for methanation is generally provided at a pressure between 30 and 50 bar. Due to the considerable pressure differential, only a relatively small quantity of motive medium is then required in order to be able to compensate for the pressure drops of the recycle gas.

If, after further compression, the product-gas stream is introduced into a useful-gas conduit system, another possible approach is to supply useful gas from the useful-gas conduit system to the ejector as the motive medium, instead of a portion of the product-gas stream. If, in particular, the useful-gas conduit system is a natural-gas transmission network, it is advantageous to effect a fine desulfurization of the useful gas supplied as the motive medium to the ejector in order to protect the catalyst from being damaged. Using the useful gas from the useful-gas conduit system as the motive medium yields the additional advantage that the ejector can be utilized to start up the plant.

The object of this invention is also a methane plant to carry out the above-described method. The methane plant comprises a reactor that contains a catalyst to effect methanation and that has an inlet attached to a supply line for synthesis gas and an outlet connected to a conduit system. An ejector is provided in a recirculation line, a suction side of the ejector is connected to the conduit system, and a pressure side of the ejector is connected to the inlet side of the reactor. At least one cooler is provided that is preferably provided in the conduit system between the reactor and the ejector in order to cool the recycle gas down to an appropriate temperature. In particular, provision can be made whereby the entire process gas stream leaving the reactor is passed through a cooler provided for generating steam.

According to the invention, the conduit system includes a compressor downstream in the flow direction of the branching point of the recirculation line, with a motive medium line discharging into a motive medium inlet of the ejector connected to the conduit system downstream of the compressor in the flow direction, or to a useful-gas conduit system for methane-containing gas, in particular, a natural-gas transmission network that is connected to the conduit system.

Since due to chemical equilibria only a limited conversion of methane is achieved in a single reactor—for example 20%—the reactor advantageously has multiple reactor stages connected in series and each holding catalyst. The invention also comprises cooling the product gas between individual reactor stages. Further additional processing steps for the synthesis gas, such as, for example drying the gas and removing $CO_2$, can also be employed depending on the specific application, these processing steps being carried out either inside or outside the reactor.

The following describes the invention with reference to a drawing that illustrates only one embodiment. Therein:

Figure 1:
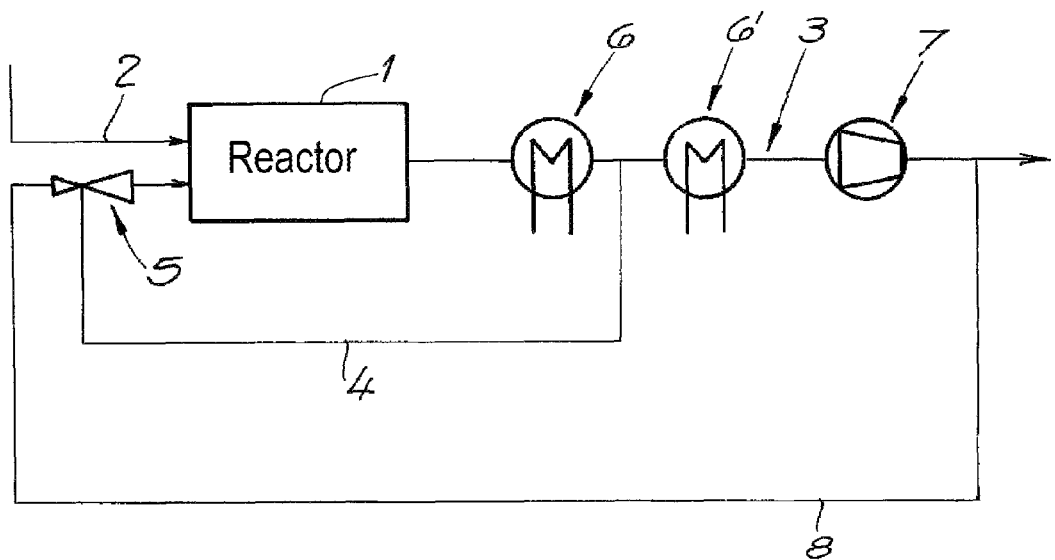
FIG. 1 shows a methane plant of making a methane-containing gas from synthesis gas.
Figure 2:
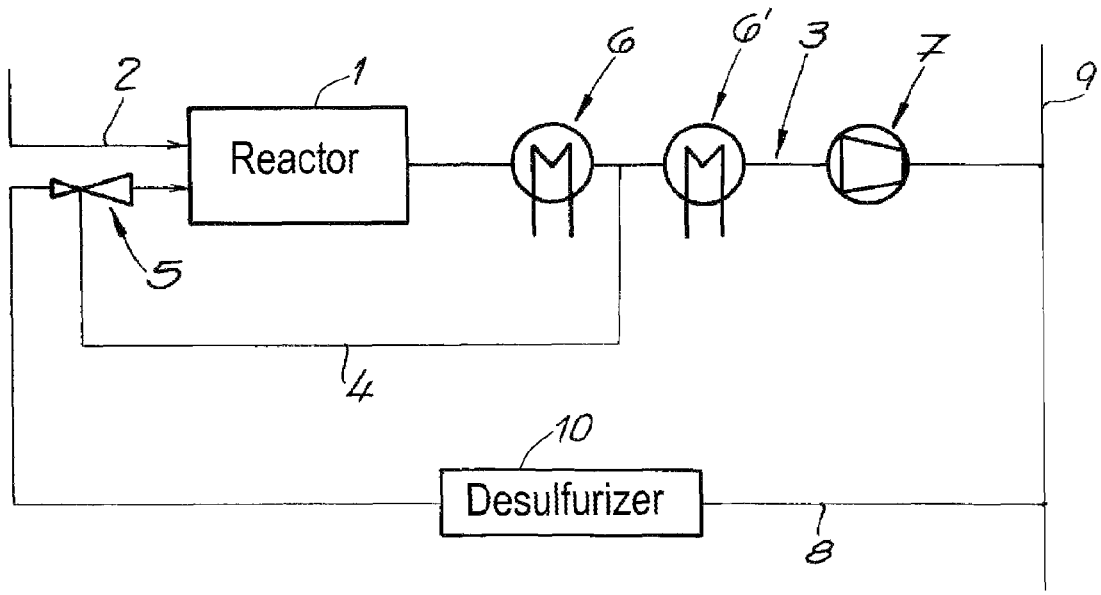
FIG. 2 shows a variant of the methane plant of FIG. 1.

FIGS. 1 and 2 show a methane plant that comprises a reactor 1 containing a catalyst for the methanation of a synthesis gas containing carbon monoxide and hydrogen. A supply line 2 for the synthesis gas is connected to the inlet of a reactor 1, and a conduit system 3 is connected to its outlet. The process gas stream leaving the reactor 1 is divided into a product-gas stream and a recycle-gas stream such that the recycle-gas stream is passed by an ejector 5 through a recirculation line 4 back to the inlet of the reactor 1. To accomplish this, the ejector 5 has a suction side connected to the conduit system 3 and a pressure side to the inlet of the reactor 1. A cooler 6 is provided in the conduit system 3 between the reactor 1 and the ejector 5.

The conduit system 3 includes a compressor 7 that is downstream in the flow direction of the branching point of the recirculation line 4 and that further compresses the product-gas stream. At least one additional cooler 6' is provided between the branching point of the recirculation line 4 and the compressor 7. This cooler functions to lower the temperature of the product-gas stream down to a level where no special design is necessary for the compressor 7 in order to accommodate high temperatures.

As shown in FIG. 1, a portion of the compressed product-gas stream is ejected downstream from the compressor 7 and passed through a motive-medium line 8 to a motive medium inlet of the ejector 5. While the synthesis gas in the supply line 2 is typically introduced into the reactor 1 at a pressure of between 30 and 50 bar, the pressure of the product gas downstream from the compressor is preferably between 60 and 80 bar. Due to the significantly higher pressure, a small portion of the product-gas stream is sufficient to move the recycle-gas stream and to compensate for the corresponding pressure drops. As indicated in FIG. 1, the portion of the product-gas stream not used as the motive medium can be fed without limitation to a pressure accumulator or to a useful-gas conduit system.

FIG. 2 shows an embodiment where, in contrast to FIG. 1, all of the product gas is compressed by the compressor 7 and then fed to a useful-gas conduit system 9, such as, for example a natural-gas transmission network. A motive-medium line 8 is connected here to a useful-gas conduit system 9. The illustrated methane plant enables, for example, synthetic natural gas (SNG) to be injected into a natural-gas transmission network. The benefit is also that the motive-medium line 8 can also be used to start up the methane plant. As indicated in FIG. 2, an apparatus 10 is provided to effect fine desulfurization in order to protect the reactor 1 from sulfur components that may be contained in the useful gas.

The invention claimed is:

1. A method of making a methane-containing gas from synthesis gas, the method comprising the steps of:
 supplying a synthesis gas containing carbon monoxide and hydrogen to a reactor holding a catalyst to effect methanation,
 dividing the process gas stream leaving the reactor into a product-gas stream and a recycle-gas stream,
 moving the recycle-gas stream through an ejector and into the reactor to be cooled,
 compressing the product-gas stream to a pressure that is greater than the pressure of the synthesis gas supplied to the reactor, and
 supplying the compressed product-gas stream as the motive medium to the ejector.

2. A method of making a methane-containing gas from synthesis gas, comprising the steps of:
 supplying a synthesis gas containing carbon monoxide and hydrogen to a reactor holding a catalyst to effect methanation,
 dividing the process gas stream leaving the reactor into a product-gas stream and a recycle-gas stream,
 moving the recycle-gas stream through an ejector and into the reactor to be cooled,
 compressing the product-gas stream to a pressure that is greater than the pressure of the synthesis gas supplied to the reactor,
 introducing the product-gas stream into a useful-gas conduit system, and
 supplying useful gas from the useful-gas conduit system as the motive medium to the ejector.

3. The method according to claim 2, wherein the useful gas supplied as the motive medium to the ejector is made to undergo fine desulfurization.

4. The method according to that claim 2, wherein the useful-gas conduit system is a natural-gas transmission network.

5. The method according to claim 1, wherein the synthesis gas is supplied to the reactor at a pressure between 30 and 50 bar.

6. The method according to claim 1, wherein the product-gas stream is compressed to a pressure between 60 and 80 bar.

7. A methane plant for making a methane-containing gas from synthesis gas, the method comprising
 a reactor holding a catalyst to effect methanation and having an inlet to which a supply line for synthesis gas is connected,
 a conduit system connected to an outlet of the reactor,
 an ejector in a recirculation line and having a suction side connected to the conduit system and a pressure side connected to the inlet of the reactor,
 at least one cooler provided in the recirculation line or in the conduit system between the reactor and the ejector,
 a compressor in the conduit system downstream in a flow direction of the branching point of the recirculation line, and
 a motive medium line that discharges into a motive medium inlet of the ejector and is connected to the conduit system downstream of the compressor in the flow direction or is connected to a useful-gas conduit system for methane-containing gas that is connected to the conduit system.

* * * * *